United States Patent [19]
Pomplun et al.

[11] Patent Number: 5,981,012
[45] Date of Patent: Nov. 9, 1999

[54] FLUSHABLE RELEASE LINER COMPRISING A RELEASE COATING ON A WATER-SENSITIVE FILM

[75] Inventors: William S. Pomplun, Neenah; Yihua Chang, Appleton; John E. Kerins, Neenah, all of Wis.

[73] Assignee: Kimberly-Clark Worldwide, Inc., Neenah, Wis.

[21] Appl. No.: 08/978,087

[22] Filed: Nov. 25, 1997

[51] Int. Cl.$^6$ ....................................... B32B 9/04
[52] U.S. Cl. ................ 428/41.8; 428/40.1; 428/364; 428/352; 428/335; 428/421; 604/364
[58] Field of Search ............................ 604/364; 428/352, 428/335, 41.8, 40.1, 421; 252/90

[56] References Cited

U.S. PATENT DOCUMENTS

| | | |
|---|---|---|
| H1340 | 7/1994 | Yetter et al. . |
| 3,515,582 | 6/1970 | Blackley .................. 117/143 |
| 3,550,592 | 12/1970 | Bernardin . |
| 3,554,788 | 1/1971 | Fechillas . |
| 3,559,650 | 2/1971 | Larson . |
| 3,575,173 | 4/1971 | Loyer ...................... 128/290 |
| 3,636,952 | 1/1972 | George . |
| 3,654,928 | 4/1972 | Duchane . |
| 3,707,430 | 12/1972 | Costanza et al. . |
| 3,855,052 | 12/1974 | Mestetsky ............... 161/167 |
| 3,881,041 | 4/1975 | Glienke . |
| 4,097,943 | 7/1978 | O'Connell . |
| 4,151,344 | 4/1979 | Doss et al. .............. 528/34 |
| 4,171,397 | 10/1979 | Morrow ................... 428/195 |
| 4,186,233 | 1/1980 | Krajewski et al. . |
| 4,229,239 | 10/1980 | Arai . |
| 4,269,650 | 5/1981 | Arai . |
| 4,282,054 | 8/1981 | Mattor et al. ............ 156/289 |
| 4,333,464 | 6/1982 | Nakano . |
| 4,348,293 | 9/1982 | Clarke et al. ............ 252/90 |
| 4,372,311 | 2/1983 | Potts . |
| 4,386,135 | 5/1983 | Campbell et al. ........ 428/447 |
| 4,416,791 | 11/1983 | Haq . |
| 4,536,434 | 8/1985 | Magnotta ................. 428/200 |
| 4,588,400 | 5/1986 | Ring et al. . |
| 4,654,395 | 3/1987 | Schulz . |
| 4,655,868 | 4/1987 | Hefele . |
| 4,705,584 | 11/1987 | Lauchenauer . |
| 4,731,143 | 3/1988 | Cross . |
| 4,900,554 | 2/1990 | Yanagibashi et al. . |
| 4,959,264 | 9/1990 | Dunk et al. ............. 428/331 |
| 5,009,647 | 4/1991 | Cross et al. ............ 604/332 |
| 5,009,652 | 4/1991 | Morgan et al. . |
| 5,061,559 | 10/1991 | Ogusi et al. ............ 428/343 |
| 5,071,648 | 12/1991 | Rosenblatt . |
| 5,082,706 | 1/1992 | Tangney .................. 428/40 |
| 5,198,299 | 3/1993 | Kato et al. ............. 428/240 |
| 5,300,358 | 4/1994 | Evers . |
| 5,332,607 | 7/1994 | Nakamura et al. ....... 428/40 |
| 5,391,423 | 2/1995 | Wnuk et al. ............ 428/217 |
| 5,405,475 | 4/1995 | Kraft et al. . |
| 5,468,807 | 11/1995 | Tsurutani et al. . |
| 5,472,518 | 12/1995 | Patnode et al. . |
| 5,509,913 | 4/1996 | Yeo . |
| 5,529,830 | 6/1996 | Dutta . |
| 5,569,348 | 10/1996 | Hefele . |
| 5,584,800 | 12/1996 | Scholz et al. . |
| 5,603,691 | 2/1997 | Scholz et al. . |
| 5,691,022 | 11/1997 | Knauf ..................... 428/40.1 |
| 5,700,571 | 12/1997 | Logue et al. ............ 428/352 |
| 5,716,685 | 2/1998 | Kumar et al. ........... 428/40.1 |

FOREIGN PATENT DOCUMENTS

| | | |
|---|---|---|
| 0 461 484 | 12/1991 | European Pat. Off. . |
| 0 479 404 | 4/1992 | European Pat. Off. . |
| 0- 532 805 A1 | 3/1993 | European Pat. Off. . |
| 63-46233 | 2/1988 | Japan . |
| 5-200375 | 8/1993 | Japan . |
| 5-228172 | 9/1993 | Japan . |
| 5-293070 | 11/1993 | Japan . |
| 7-70525 | 3/1995 | Japan . |
| WO 94/23769 | 10/1994 | WIPO . |
| WO 96 20831 | 7/1996 | WIPO . |
| WO 97 18082 | 5/1997 | WIPO . |
| WO 99 08727 | 2/1999 | WIPO . |

OTHER PUBLICATIONS

JP 06 100845, Apr. 12, 1994, Abstract.
JP 07 003699, Jan. 6, 1995, Abstract.
JP 06 126901, May 10, 1994, Abstract.
JP 06 134910, May 17, 1994, Abstract.

*Primary Examiner*—David W. Wu
*Assistant Examiner*—Caixia Lu-Rutt
*Attorney, Agent, or Firm*—Jones & Askew, LLP

[57] ABSTRACT

The present invention is directed to a flushable release liner. The flushable release liner is formed by applying a release coating onto at least one surface of a water-sensitive film. The flushable release liner maintains its integrity and strength when in use, but disperses when placed in contact with water, such as in a conventional sink or toilet. Moreover, the present invention is directed to water-dispersible products, including flushable products, which contain the flushable release liner.

20 Claims, No Drawings

FLUSHABLE RELEASE LINER COMPRISING A RELEASE COATING ON A WATER-SENSITIVE FILM

FIELD OF THE INVENTION

The present invention is directed to a flushable release liner. The flushable release liner is formed by applying a release coating onto at least one surface of a water-sensitive film. The flushable release liner maintains its structural integrity and strength when in use, but disperses when placed in contact with water, such as in a conventional sink or toilet. Moreover, the present invention is directed to products, including flushable and non-flushable products, which contain the flushable release liner.

BACKGROUND OF THE INVENTION

Disposable products have revolutionized modern lifestyle and are of great convenience to society. Such products generally are relatively inexpensive, sanitary and quick and easy to use. Disposal of such products, however, is a concern as landfills close and incineration contributes to urban smog and pollution. Consequently, there is an urgent need for disposable products that can be disposed of without dumping or incineration. An ideal disposal alternative would be the use of municipal sewage treatment plants and private residential septic systems. Products suited for disposal in sewage systems that can be flushed down a conventional toilet are termed "flushable." An essential feature of flushable products is that they must have sufficient strength for their intended use, yet lose structural integrity upon contact with water.

Numerous consumer products, which were formerly unable to be disposed of in a conventional toilet, are made flushable today. Such products include water-soluble films, wipes, tampon applicators, etc. However, many consumer products have remained unflushable.

One such product that has remained unflushable to date is release liners. Release liners are used to temporarily cover an adhesive layer before use in many personal care products. The release liner provides protection for the adhesive layer against exposure to materials, which might negatively affect the ability of the adhesive strip to adhere to a desired substrate, and provides protection against undesired, premature adhesion to a substrate. Conventional release liners comprise a paper substrate coated with a release coating. The release coating is formulated to provide very little adhesion of the coated paper to any other substrate, particularly pressure-sensitive, hot-melt adhesives, so the release liner may be easily removed from the adhesive strip without disturbing the adhesive strip. Typically, release coatings comprise a silicone-containing polymeric material.

Release liners are used in many personal care products. For example, many sanitary napkins have an adhesive strip on the backside of the napkin (the napkin surface opposite to the body-contacting surface) to fix the napkin to an undergarment and hold the napkin in place against the body. Before use, the adhesive strip is protected with a peelable release liner. Once removed, the peelable release liner must be discarded. Since peelable release liners are typically silicone-coated paper, the release liners do not disperse in water; consequently, disposal options are limited to depositing the release liner in a trash receptacle. Although disposing of conventional release liners in a toilet would be convenient to the consumer, such disposal potentially creates blockages in the toilet or household sewer line.

What is needed in the art is a flushable release sheet, which can be discarded and then flushed in a conventional toilet. Such a flushable release liner would offer convenience to the consumer, and not cause problems such as blockages in the sewage transport process.

SUMMARY OF THE INVENTION

The present invention is directed to a flushable release liner comprising a thin release coating on at least one surface of a water-sensitive film. The coated water-sensitive film functions like conventional release papers currently used. Conventional release papers comprise a peelable coated paper, which covers the adhesive strip on a feminine sanitary napkin. Unlike conventional release papers, the coated water-sensitive film of the present invention rapidly loses integrity and strength when discarded in a conventional toilet. Without the support of the water-sensitive film, the thin release coating readily breaks up under the force of flushing. The two-layer structure of the flushable release liner offers the performance of a paper-based release liner with the additional option of disposal in a toilet and of potentially lower cost.

The present invention is also directed to a method of preparing a flushable release sheet. The method comprises coating a thin layer of polymer having release characteristics onto a base film, wherein the base film comprises a water-sensitive polymer. When dry, the two-layer laminate displays mechanical features comparable to a conventional coated paper liner. The base film itself may be manufactured, taking into consideration variables such as film thickness, molecular weight, and blending additives, to control the functionality of the plastic film. The polymeric coating controls the release characteristics of the plastic film. The coating is formulated to provide very little adhesion to many substrates, particularly pressure-sensitive, hot-melt adhesives, so that the coating may be easily removed from an adhesive strip without disturbing the adhesive strip, while having high adhesion to the water-sensitive substrate. The coating formulation ensures that the two-layer polymer film peels at the surface of the release coating, not at the interface between the coating and the water-sensitive base film.

The present invention is also directed to articles containing the flushable release liner. Specifically, the flushable release liners of the present invention are useful in connection with a variety of products, and especially absorbent products such as sanitary napkins, panty liners, diapers, dressings and the like. Although the release liner of the present invention finds particular use in the above-mentioned products, the concept of a flushable release liner has potential for any other application requiring a release material.

The present invention provides a mechanism for eliminating disposal problems associated with various consumer products. A nonlimiting detailed description of the invention and examples of specific embodiments are provided below.

DETAILED DESCRIPTION OF THE INVENTION

The present invention is directed to a flushable release liner comprising a thin release coating on at least one surface of a water-sensitive film. The coated water-sensitive film functions like conventional release papers currently used. However, unlike conventional release papers, the coated water-sensitive film of the present invention is "flushable." As used herein, the term "flushable" describes a product which rapidly loses integrity and strength when discarded in a conventional sink or toilet. The flushable feature of the two-layer laminate of the present invention comes from the water-sensitivity of the base film and the low strength of the thin release coating. When immersed in water, the uncoated side of the base film readily wets and weakens. The water-sensitive film quickly loses integrity and strength when exposed to water. When the substrate layer loses its mechanical integrity, the release coating, which is thin and mechanically weak, readily disperses under the flushing force of a toilet or the force of water flow in a sink.

The two-layer laminate of the present invention is prepared by any process wherein a thin layer of polymer, having release characteristics, is uniformly and continuously coated onto at least one surface of a water-sensitive film, such as a polyethylene oxide (PEO) film. Suitable coating processes include, but are not limited to, extrusion coating, solvent-base coating, and hot-melt coating. Suitable extrusion coating techniques include, but are not limited to, curtain extrusion coating and co-extrusion of the coating and the water-sensitive film. Suitable solvent-base coating techniques include, but are not limited to, spray coating. Suitable hot-melt coating techniques include, but are not limited to, slot coating, spray coating and gravure coating. Desirably, the coating process is a hot-melt slot coating process or an extrusion coating process. At least a portion of the surface area of the water-sensitive film is left uncoated so that the two-layer laminate remains flushable. One coating process is described below.

Molten "release polymer" is delivered from a melting tank through a heated hose to a slot die. As used herein, the term "release polymer" describes a polymer which possesses release characteristics. The temperature of the melting tank, hose and slot die may vary depending upon the melt rheology of the release polymer in the coating process. The molten polymer is uniformly applied directly onto the water-sensitive film, or alternatively, onto a carrier substrate and subsequently transferred onto the water-sensitive film. Line speeds may vary depending upon the "open time" of the release polymer. As used herein, the "open time" of a polymer refers to the amount of time required for the polymer to loose its tackiness.

In a transfer coating process, the coated carrier substrate moves further through the process and comes into contact with the water-sensitive film, which is properly aligned with the coated carrier substrate. The coating is transferred from the carrier substrate to the water-sensitive film under pressure as the film and carrier substrate pass through a nip roll. In practice, optimum coating thickness is achieved by adjusting processing factors which include, but are not limited to, the release polymer, the coating temperature, the resin flow rate, line speed, and the pressure applied at the nip roll.

In either the direct coating process or the transfer coating process, the adhesion of the release coating to the water-sensitive film should be greater than the adhesion of the release coating to the screen (direct coating) or the carrier substrate (transfer coating). The choice of release polymer should take into consideration the desired release characteristics and adhesion properties of the release polymer. The release polymer should have good adhesion to the water-sensitive substrate. Suitable release polymers for use in the present invention include any processible polymer with appropriate melt rheology, release characteristics and adhesion properties for application by the above-described hot melt coating process. Suitable polymers include, but are not limited to, polyolefins, fluoropolymers, and silicones.

One or more of the release polymers above may be combined to form the coating of the water-sensitive film.

Further, the release polymer may contain one or more of the following additives including, but not limited to, compatibilizers, processing aids, plasticizers, tackifiers, detackifiers, slip agents, and anti-microbial agents, as fabricating agents or as modifiers depending on the specific properties desired in the coating and the final product. The coating should be formulated to provide little adhesion to a variety of substrates, particularly pressure-sensitive, hot-melt adhesives, so that the coating may be easily removed from an adhesive strip without disturbing the adhesive strip, while having high adhesion to the water-sensitive substrate. The coating formulation ensures that the two-layer polymer film peels at the surface of the release coating, not at the interface between the coating and water-sensitive base film.

Desirably, the release polymer is a polyalphaolefin having a melt viscosity of about 400 to about 8,000 cps at 190° C. Suitable polymers include, but are not limited to, amorphous ethylene-propylene copolymers. Particularly suitable polymers are manufactured by the U.S. Rexene Company under the tradename REXTAC®. One REXTAC® resin, RTE32, is particularly suitable for the present invention. In a further embodiment, one or more REXTAC® resins are blended with a low molecular weight, highly branched polyolefin to reduce the tackiness of the hydrophobic polymer coating. Desirably, the highly branched polyolefin has a number-average molecular weight ($M_n$) of less than about 2800. A particularly suitable low molecular weight, highly branched polyolefin, VYBAR® 253 ($M_n$=520), is manufactured by the Petrolite Corporation. Blends of REXTAC® and VYBAR® 253 provide good results as release coating materials. Desirably, the ratio of REXTAC® resin to VYBAR® 253 is from about 100/0 wt/wt to about 70/30 wt/wt. More desirably, the ratio of REXTAC® resin to VYBAR® 253 is from about 98/2 wt/wt to about 75/25 wt/wt. Most desirably, the ratio of REXTAC® resin to VYBAR® 253 is from about 95/5 wt/wt to about 80/20 wt/wt. Particularly useful blends are RTE32/VYBAR® 253 (95/5 wt/wt) and RTE32/VYBAR® 253 (80/20 wt/wt).

The thickness of the release coating may vary greatly depending upon the end use of the two-layer laminate and/or products containing the two-layer laminate. However, film thickness should be minimized when possible to reduce product cost and to reduce the mechanical strength of the coating, particularly for flushable products, so that the coating will disperse due to the flushing forces of water on the coating. Desirably, the release coating thickness will be less than about 1.0 mil. (25.4 micrometers). More desirably, the release coating thickness will be less than about 0.6 mil. (15.2 micrometers). Most desirably, the release coating thickness will be less than about 0.2 mil. (5.1 micrometers). However, the coating should be thick enough to provide a continuous coating along the film surface.

The carrier substrate used in the above-described process may be any substrate which can transfer the release coating to the water-sensitive film. Suitable carrier substrates display little or no adhesion with the release coating relative to the adhesion between the water-sensitive film and the release coating. Suitable carrier substrates include, but are not limited to, release paper, release films, and release-coated substrates such as fabrics and/or belts. Desirably, the carrier substrate is a release paper. More desirably, the carrier substrate is an AKROSIL® High Release Paper.

Water-sensitive films for use in the present invention include any water-sensitive film capable of withstanding the above-described coating processes. As used herein, the phrase "water-sensitive film" describes films, which lose integrity over time when in the presence of water and includes, but is not limited to, water-soluble films and water-dispersible films. Suitable water-sensitive films have sufficient strength and adhesion properties for use in the above-described processes. Suitable polymers include, but are not limited to, polyalkylene oxides, such as polyethylene oxide (PEO) and ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), and poly (2,4-dimethyl-6-triazinyl ethylene).

The water-sensitive film of the present invention may be made entirely of water-sensitive polymeric material or may contain water-sensitive as well as water-insoluble materials so long as the film dissolves or disperses in water, such as in a conventional toilet. Additionally, water-sensitive films may also be made by combining various different types of water-sensitive film materials. In some embodiments, it may be desirable to employ one or more additives into the water-sensitive film material including, but not limited to, compatibilizers, processing aids, plasticizers, tackifiers, detackifiers, slip agents, and anti-microbial agents, as fabricating agents or as modifiers depending on the specific properties desired in the film and the final product.

Desirably the water-sensitive film of the present invention comprises a polyalkylene oxide film or a polyvinyl alcohol film. More desirably, the water-sensitive film of the present invention comprises a polyethylene oxide film, an ethylene oxide/propylene oxide copolymer film or a polyvinyl alcohol film. More desirably, the water-sensitive film of the present invention comprises a polyethylene oxide film or a polyvinyl alcohol film. The polyethylene oxide film is the most desirable film for the transfer coating procedure, while the polyvinyl alcohol film is the most desirable film for the direct coating procedure.

The thickness of the water-sensitive film may vary greatly depending upon the end use of the two-layer laminate and/or products containing the two-layer laminate. Film thickness should be minimized when possible to reduce product cost and to reduce the time necessary for the film to disperse, especially in the case of flushable products. Desirably, the water-sensitive film thickness will be less than about 2.0 mil (50.8 micrometers). More desirably, the water-sensitive film thickness will be from about 0.1 mil (2.5 micrometers) to about 1.4 mil (35.6 micrometers). Most desirably, the water-sensitive film thickness will be from about 0.1 mil (2.5 micrometers) to about 0.5 mil (12.7 micrometers).

With release characteristics and adhesion properties, the two-layer laminate of the present invention finds applicability in a variety of articles. Specifically, the flushable release liners of the present invention are useful in connection with a variety of products, and especially absorbent products such as sanitary napkins, diapers, dressings and the like. Although the release liner of the present invention finds particular use in the above-mentioned products, the concept of a flushable release liner has potential for any other applications wherein a release liner is used.

Those skilled in the art will readily understand that the two-layer laminates of the present invention may be advantageously employed in the preparation of a wide variety of products designed to contain at least one component having a release surface. Such products may comprise only the coated water-sensitive film or may comprise a coated water-sensitive film in combination with one or more additional layers such as coatings, films, fabrics, etc. Although the coated water-sensitive film of the present invention is particularly suited for release liners, the coated water-sensitive film of the present invention may be advantageously employed in the preparation of a wide variety of consumer products other than release liners.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

A release liner was made by the following process. A release coating comprising a blend of 30 wt % of a low molecular weight paraffin wax, VYBAR® 253 (Petrolite Polymers), and a coating-grade polyalphaolefin, REXTAC® RTE32 (U.S. Rexene Company), was coated onto a base film of polyethylene oxide (PEO). The blend was slot coated onto a high release paper and subsequently transferred to the PEO film under the following conditions: tank temperature, 315° F.; grid temperature, 324° F.; hose temperature, 340° F.; die temperature, 330° F.; and line speed, 24 ft/min. The base film of PEO, roughly 1.2 mil (30.5 micrometers) thick, was prepared from resin compounded at Planet Polymer (San Diego, Calif.). The blend was applied the PEO film to produce a final coating thickness of about 0.8 mil (20.3 micrometers).

The base Rexene resin itself showed good adhesion to the PEO substrate, although slightly tacky. When blended with the VYBAR® additive, the adhesion with the PEO substrate was improved while the tack of the coating was effectively suppressed.

Since Rexene resins themselves are used as a base component in many adhesives formulations, the resulting two-layer laminate was tested for adhesion to Rexene resins. The blend showed no adhesion to a coating of unblended RTE32. The blend also showed no adhesion to other Rexene coatings, such as a REXTAC® RT2330 coating.

The two-layer laminate readily broke up when held under gently flowing water from a sink tap. The resulting two-layer laminate displayed the key features required in a flushable release sheet.

What is claimed is:

1. A flushable laminate having release characteristics, said laminate consisting essentially of:
   a water-sensitive film; and
   a continuous release coating of polymeric material on a surface of the water-sensitive film, wherein the coating adheres to the water-sensitive film and provides release characteristics to the laminate;
   wherein the polymeric material comprises at least one polyalphaolefin having a melt viscosity of about 400 to about 8000 cps at 190° C.

2. The flushable laminate of claim 1, wherein the water-sensitive film comprises polyethylene oxide, ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene) or a combination thereof.

3. The flushable laminate of claim 2, wherein the water-sensitive film comprises polyethylene oxide, ethylene oxide-propylene oxide copolymer, polyvinyl alcohol or a combination thereof.

4. The flushable laminate of claim 1, wherein the coating further comprises at least one low molecular weight, highly branched polyolefin, wherein the at least one low molecular weight, highly branched polyolefin has a number-average molecular weight of less than about 2800.

5. The flushable laminate of claim 3, wherein the water-sensitive film comprises polyethylene oxide.

6. The flushable laminate of claim 5, wherein the flushable laminate is a release liner.

7. The flushable laminate of claim 1, wherein the water-sensitive film has a thickness of less than about 2.0 mil (50.8 micrometers) and the coating has a thickness of less than about 1.2 mil (30.5 micrometers).

8. A flushable release liner consisting essentially of:
   a water-sensitive film; and
   a continuous release coating of polymeric material on a surface of the water-sensitive film, wherein the coating adheres to the water-sensitive film and provides release characteristics to the liner;
   wherein the polymeric material comprises at least one polyalphaolefin having a melt viscosity of about 400 to about 8000 cps at 190° C.

9. The flushable release liner of claim 8, wherein the water-sensitive film comprises polyethylene oxide, ethylene oxide/propylene oxide copolymers, polymethacrylic acid, polymethacrylic acid copolymers, polyvinyl alcohol, poly (2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene) or a combination thereof.

10. The flushable release liner of claim 9, wherein the water-sensitive film comprises polyethylene oxide, ethylene oxide-propylene oxide copolymer, polyvinyl alcohol or a combination thereof.

11. The flushable release liner of claim 9, wherein the coating further comprises at least one low molecular weight, highly branched polyolefin, at least one low molecular weight, highly branched polyolefin has a number-average molecular weight of less than about 2800.

12. The flushable release liner of claim 10, wherein the water-sensitive film comprises polyethylene oxide.

13. The flushable release liner of claim 8, wherein the water-sensitive film has a thickness of less than about 2.0 mil (50.8 micrometers) and the coating has a thickness of less than about 1.2 mil (30.5 micrometers).

14. A product comprising:
   a flushable laminate, wherein the flushable laminate comprises a water-sensitive film and a continuous release coating of polymeric material on a surface of the water-sensitive film, wherein the coating adheres to the water-sensitive film and provides release characteristics to the laminate; and
   at least one additional layer adhered to the continuous release coating of the laminate;
   wherein the product comprise a disposable a disposable adsorbent article, a sanitary napkin, a dressing, a panty liner, an incontinence garment, a bandage or a diaper.

15. The product of claim 14, wherein the product comprises a disposable absorbent article, said disposable article further comprising a liquid previous topsheet and a liquid impervious backsheet.

16. A method of making a flushable laminate having release characteristics, said method consisting essentially of:
   coating a continuous release layer of polymeric material onto a surface of a water-sensitive film, wherein the release layer adheres to the water-sensitive film and provides release characteristics to the laminate;
   wherein the polymeric material comprises at least one polyalphaolefin having a melt viscosity of about 400 to about 8000 cps at 190° C.

17. The method of claim 16, further comprising at least one low molecular weight, highly branched polyolefin, wherein the at least one low molecular weight, highly branched polyolefin has a number-average molecular weight of less than about 2800.

18. The method of claim 16, wherein the water-sensitive film is a film material comprising polyethylene oxide, ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene) or a combination thereof.

19. The method of claim 18, wherein the polymeric material and the film material are co-extruded to form the flushable laminate.

20. The method of claim 16, wherein the laminate is formed by extrusion coating or hot-melt slot coating.

* * * * *